US010195748B2

(12) United States Patent
Uetabira (10) Patent No.: US 10,195,748 B2
(45) Date of Patent: Feb. 5, 2019

(54) HUMANOID ROBOT (71) Applicant: INTERMAN Corporation, Kagoshima (JP)

(72) Inventor: Shigeki Uetabira, Kagoshima (JP)

(73) Assignee: INTERMAN Corporation, Kagoshima (JP)

( * ) Notice: Subject to any disclaimer, the term of this patent is extended or adjusted under 35 U.S.C. 154(b) by 166 days.

(21) Appl. No.: 15/508,443

(22) PCT Filed: Aug. 31, 2015

(86) PCT No.: PCT/JP2015/074739
§ 371 (c)(1),
(2) Date: Mar. 2, 2017

(87) PCT Pub. No.: WO2016/035759
PCT Pub. Date: Mar. 10, 2016

(65) Prior Publication Data
US 2017/0282380 A1   Oct. 5, 2017

(30) Foreign Application Priority Data

Sep. 3, 2014 (JP) .................. 2014-179226

(51) Int. Cl.
B25J 15/12 (2006.01)
A61B 5/00 (2006.01)
(Continued)

(52) U.S. Cl.
CPC .............. B25J 15/12 (2013.01); A61B 5/117 (2013.01); A61B 5/489 (2013.01); A61B 5/6825 (2013.01);
(Continued)

(58) Field of Classification Search
CPC ........ B25J 15/12; B25J 9/0006; B25J 13/088; B25J 15/0009; B25J 13/085; B25J 19/02;
(Continued)

(56) References Cited

U.S. PATENT DOCUMENTS 5,967,580 A * 10/1999 Rosheim .................... B25J 3/04
294/106
9,545,717 B2 * 1/2017 Kim ...................... B25J 9/1612
(Continued)

FOREIGN PATENT DOCUMENTS

JP   2001-236585 A   8/2001
JP   2003-281653 A   10/2003
(Continued)

OTHER PUBLICATIONS

Japanese Office Action dated Oct. 3, 2017 from corresponding Japan application No. 2016-546641; 5pgs.
(Continued)

Primary Examiner — Jaime Figueroa
(74) Attorney, Agent, or Firm — Maier & Maier, PLLC (57) ABSTRACT A humanoid robot capable of identifying an individual in a natural way is described. This humanoid robot shakes a hand of a person to acquire biological information of the person and identify the individual person. Particularly, a near infrared light emitting device and a near infrared sensor are installed in a hand of the humanoid robot to irradiate a hand of a human being with near infrared light emitted from the near infrared light emitting device and detect a vein pattern by the near infrared sensor. The individual person can be identified by recording and collating this vein pattern.

9 Claims, 7 Drawing Sheets (51) Int. Cl.
*B25J 15/00* (2006.01)
*A61B 5/117* (2016.01)
*B25J 9/00* (2006.01)
*B25J 9/16* (2006.01)
*B25J 13/08* (2006.01)
*B25J 19/02* (2006.01)

(52) U.S. Cl.
CPC ........... *B25J 9/0006* (2013.01); *B25J 9/1612* (2013.01); *B25J 9/1694* (2013.01); *B25J 13/085* (2013.01); *B25J 13/088* (2013.01); *B25J 15/0009* (2013.01); *B25J 19/02* (2013.01)

(58) Field of Classification Search
CPC ..... B25J 9/1694; B25J 9/1612; A61B 5/6825; A61B 5/489; A61B 5/117
USPC ......................................................... 700/245
See application file for complete search history.

(56) References Cited

U.S. PATENT DOCUMENTS

| | | | | |
|---|---|---|---|---|
| 9,814,604 | B2* | 11/2017 | Jury | A61F 2/583 |
| 2006/0129278 | A1* | 6/2006 | Sugiyama | B25J 13/085 |
| | | | | 700/245 |
| 2009/0227925 | A1* | 9/2009 | McBean | A61F 5/0127 |
| | | | | 602/16 |
| 2010/0176615 | A1* | 7/2010 | Okuda | A61F 2/583 |
| | | | | 294/106 |
| 2010/0259057 | A1* | 10/2010 | Madhani | B25J 9/1045 |
| | | | | 294/106 |

FOREIGN PATENT DOCUMENTS

| | | |
|---|---|---|
| JP | 2005-193351 A | 7/2005 |
| JP | 2006-167841 A | 6/2006 |
| JP | 2006-235772 A | 9/2006 |
| JP | 2006-255430 A | 9/2006 |
| JP | 2008-262272 A | 10/2008 |
| JP | 2011-81756 A | 4/2011 |
| JP | 2011-240468 A | 12/2011 |
| JP | 2014-94436 A | 5/2014 |

OTHER PUBLICATIONS

International Search Report and Written Opinion dated Dec. 8, 2015 of corresponding application No. PCT/JP2015/074739, 6pgs.

Henze, B.; Werner, A.; Roa, M.A.; Garofalo, G.; Englsberger, J.; Ott, C., Control applications of TORO—A Torque controlled humanoid robot, Proceedings of 2014 14th IEEE-RAS International Conference on Humanoid Robots (Humanoids), Nov. 2014, pp. 841-841; 2 pgs.

Shiomi, M.; Kanda, T.; Ishiguro, H.; Hagita, N., Interactive Humanoid Robots for a Science Museum, IEEE Intelligent Systems, vol. 22, Issue:2, Mar. 2007, pp. 25-32; 7 pgs.

* cited by examiner

HUMANOID ROBOT

FIELD OF THE INVENTION

The present invention relates to a humanoid robot capable of identifying an individual in a natural way.

BACKGROUND ART

Typical practical robots are industrial robots which are used in the manufacturing industry or the like. However, in recent years, humanoid robots capable of communicating with human beings are being made into products. Underlying this has been the progress of complicated techniques such as speech recognition, voice synthesis and the like. Also, a robot having high autonomy and availability in home can be realized by improvement in the functionality of audio-visual instruments and development of computer technology for effectively processing external information.

This type of a humanoid robot is usually capable of autonomously moving to a position required for following an instruction by a person with two legs or wheels. Furthermore, it is expected that a robot is capable of performing field works and activities alone.

PRIOR ART LITERATURE

Patent Document

[Patent Document 1] Japanese Patent Published Application No. 2014-94436

SUMMARY OF INVENTION

Problems to be Solved by the Invention

However, when such autonomous humanoid robots have been generally used, it is needed to deal with the problem of theft. If the stolen robot can work properly, it merely encourage theft. In addition to this, there is the possibility that privacy of the owner leaks through a robot.

On the other hand, it can be conceived that a robot can start operation only through authentication in the same manner as a personal computer is used. For example, Patent Document 1 describes a humanoid robot which performs a predetermined work when an authorized operator is authenticated. However, in accordance with this technique, authentication is not performed by the humanoid robot itself but performed by the operator with another authentication device, so that it is not natural as a humanoid robot expected to make communication with a human being, and the use of such another authentication device is not user friendly as a household appliance. Furthermore, this authentication process is not smart as an authentication process for a humanoid robot capable of making communication with a human being and provided for the purpose of relaxing and entertaining a person through operation of the robot so that original attraction is reduced by half.

It is therefore an object of the present invention to provide a humanoid robot capable of identifying individuals encountering the humanoid robot through a natural motion of the robot itself.

Means to Solve the Problems

In order to accomplish the object as described above, a humanoid robot comprises: a right hand having a plurality of finger members provided with joints and drive mechanisms and capable of performs a handshake with a hand of a human being; a near infrared light emitting device and a near infrared sensor which are installed in the right hand and located in such positions that, while the right hand is shaking the hand of the human being, near infrared light emitted from the near infrared light emitting device irradiates the inside of the hand of the human being and is detected by the near infrared sensor as a vein pattern; an information recording device configured to record the vein pattern detected by the near infrared sensor; and an information processing apparatus configured to compare and process the vein pattern recorded in the information recording device and another vein pattern detected by the near infrared sensor to calculate a similarity degree therebetween.

In accordance with a preferred embodiment, the information processing apparatus controls the motion of the right hand of the humanoid robot to shake the hand of the human being, acquires a vein pattern by the near infrared light emitting device and the near infrared sensor as a collation data set, calculates the similarity degree between this vein pattern and the vein pattern which is recorded in advance as a registration data set in the information recording device, and performs personal identification of the human being on the basis of this similarity degree.

Also, in accordance with a preferred embodiment, the vein pattern which is recorded as a registration data set is a vein pattern of an owner of the humanoid robot, and owner authentication is performed on the basis of the similarity degree between this vein pattern and the collation data set.

Furthermore, in accordance with a preferred embodiment, the registration data set is repeatedly acquired while changing the position of the right hand of the humanoid robot.

Still further, in accordance with a preferred embodiment, after acquiring the registration data set, the right hand of the humanoid robot is released from the hand of the human being and shakes the hand of the human being again to acquire the registration data set again, wherein both the previous registration data set and the registration data set acquired again are used as the registration data sets for performing personal identification by comparing and processing the registration data sets with the collation data set.

Still further, in accordance with a preferred embodiment, the result of personal identification is reflected in the behaviour of the humanoid robot.

Still further, in accordance with a preferred embodiment, the vein pattern is a vein pattern of a finger of the human being.

Effects of the Invention

In accordance with the humanoid robot of the present invention, it is possible to inhibit theft of the humanoid robot and reflect identification of an individual in the behaviour of the humanoid robot by identifying the individual through handshake which is a natural motion of a person. Accordingly, a humanoid robot having high communication abilities with a human being can be realized.

MODES FOR CARRYING OUT THE INVENTION

Figure 1:
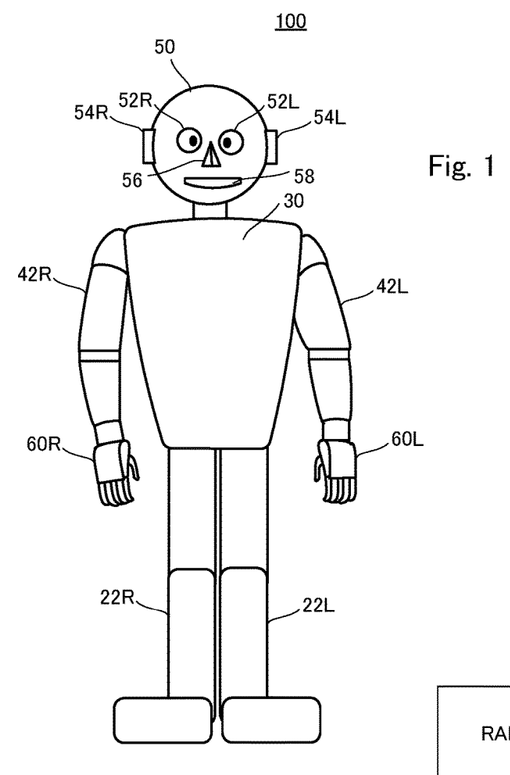
FIG. 1 is a schematic diagram for showing a basic structure of a humanoid robot in accordance with the present invention.

In what follows, humanoid robots in accordance with several embodiments of the present invention will be explained with reference to the accompanying drawings. FIG. 1 is a schematic diagram for showing a basic structure of a humanoid robot. This humanoid robot 100 is provided with a left leg 22L, a right leg 22R, a torso 30, a left arm 42L, a right arm 42R, a head 50.

The left arm 42L and the right arm 42R on either side of the torso 30 are provided with a plurality of joints, drive mechanisms of the joints, torque sensors, joint position sensors for detecting positions of the joints and acceleration sensors so that same motions can be performed as human arms.

The head 50 is implemented with left and right eyes 52L and 52R incorporating image sensors respectively, left and right ears 54L and 54R incorporating microphones respectively, a nose 56 incorporating a smell sensor, and a mouth 58 incorporating a speaker.

The left leg 22L and the right leg 22R connected to the bottom of the torso 30 are provided with a plurality of joints, drive mechanisms of the joints, torque sensors, joint position sensors for detecting positions of the joints and acceleration sensors so that same motions can be performed as human legs. However, even if these legs are formed in a more simplified structure, the features of the embodiment of the present invention can be applied as described below. For example, the present invention can be applied also in the case where a left leg and a right leg are not separated but united with a plurality of wheels installed in a bottom portion thereof so that a humanoid robot can move by rotating these wheels.

Figure 2:
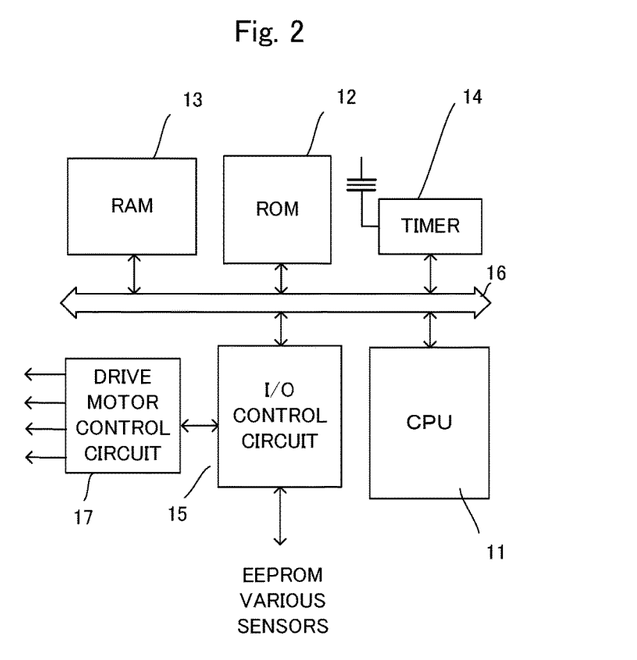
FIG. 2 is a block diagram showing a main portion of an information processing apparatus for controlling the operation of the humanoid robot shown in FIG. 1.

In addition to this, an information processing apparatus is provided in an appropriate position in the humanoid robot 100 for controlling the operation of this humanoid robot 100. FIG. 2 is a block diagram showing a main portion of this information processing apparatus 10. This information processing apparatus 10 includes a CPU 11, a ROM 12, a RAM 13, a timer 14 and an I/O control circuit 15 which are interconnected through a bus 16. The CPU 11 starts operation by running a program stored in the ROM 12 and controls the operation of the humanoid robot 100 by reading and storing data in the RAM 13, outputting commands to the I/O control circuit 15 and the like with reference to the interrupt request signal from the timer 14 and the like.

The I/O control circuit 15 directly controls external devices such as a drive motor control circuit 17 by outputting control signals to the external devices in accordance with instructions output from the CPU 11 to realize actual operations in accordance with the program. The drive motor control circuit 17 controls power supply to motors which moves the joints of the humanoid robot 100.

The external devices controlled by the I/O control circuit 15 include, besides the drive motor control circuit 17, a nonvolatile memory such as an EEPROM, a driving power transmission mechanism, a GPS, a wireless LAN, a temperature sensor, a humidity sensor, a position sensor, a battery and so forth. Furthermore, the external devices include a near infrared LED and a near infrared sensor to be described below.

Incidentally, while the information processing apparatus controls the drive mechanisms for moving the left leg 22L, the right leg 22R, the torso 30, the left arm 42L, the right arm 42R and the head 50 of the humanoid robot 100, the details of the structure of the drive mechanisms and the control process thereof are generally known so that detailed explanation is omitted except those specifically described below.

[Embodiment 1]

Figure 3:
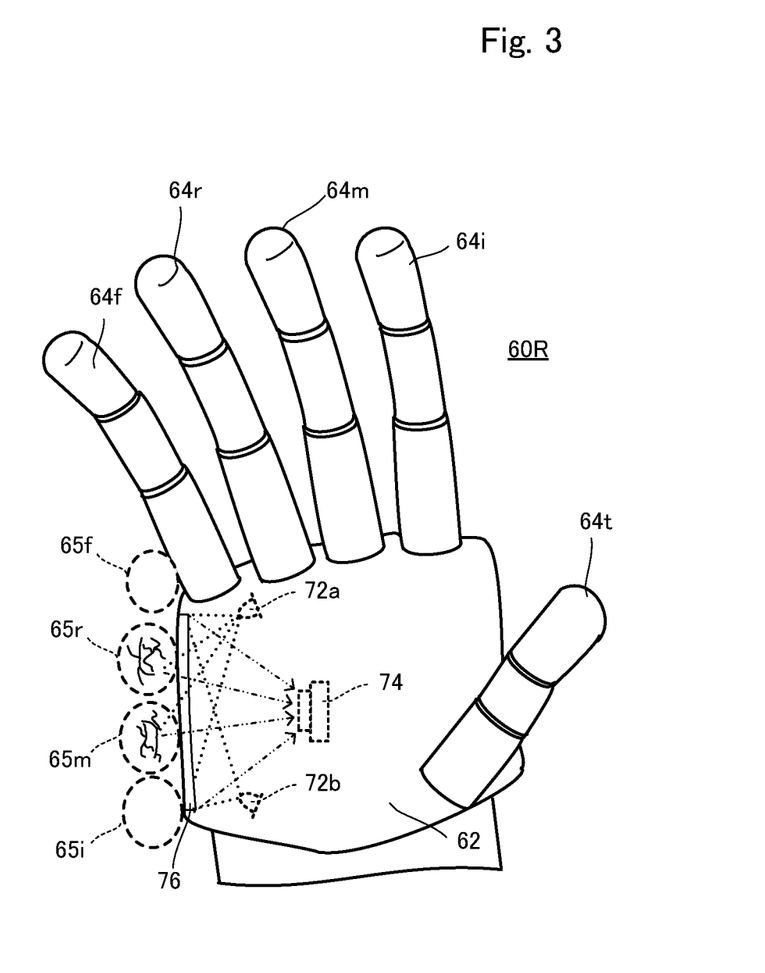
FIG. 3 is a schematic diagram for showing the structure of a hand of the humanoid robot in accordance with an embodiment 1.
Figure 4:
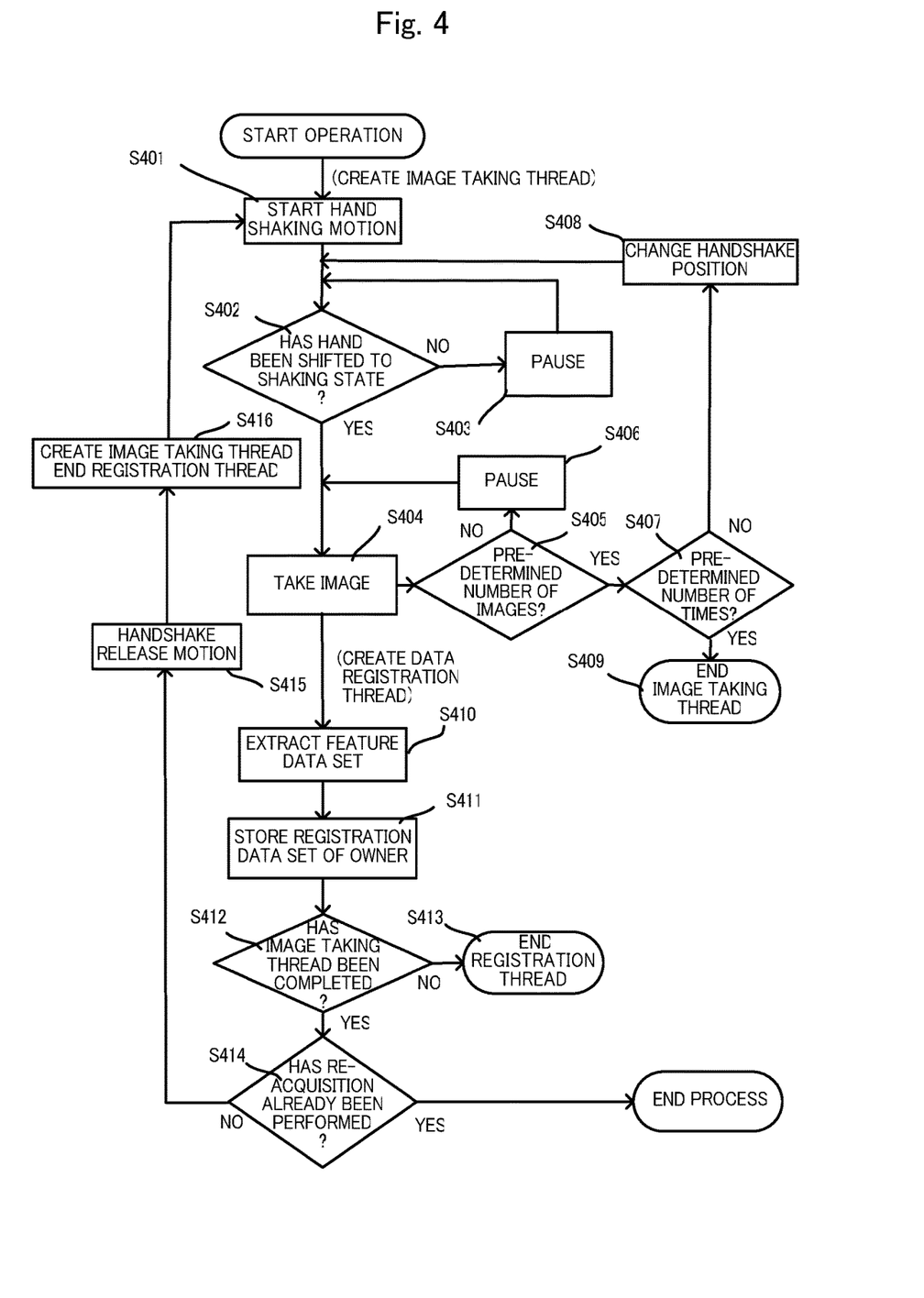
FIG. 4 is a flow chart for showing the procedure of registering an owner vein data set by shaking hands with a human being in accordance with the humanoid robot of the embodiment 1.
Figure 5:
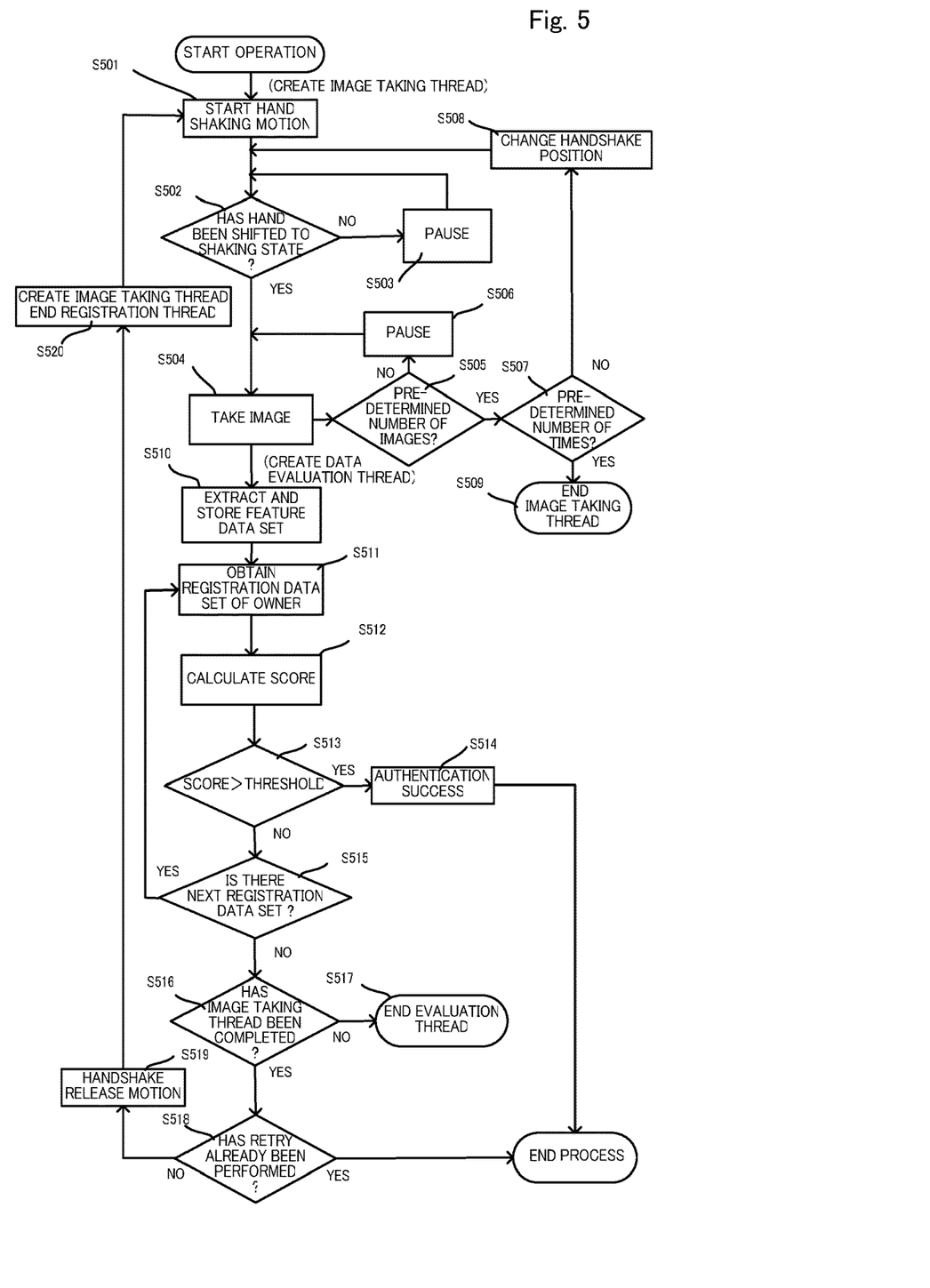
FIG. 5 is a flow chart for showing the procedure of performing authentication of the owner by shaking hands with a human being in accordance with the humanoid robot of the embodiment 1 of the present invention.

Referring to FIG. 3 through FIG. 5, a humanoid robot of an embodiment 1 will be explained. The basic structure of this humanoid robot is as illustrated in FIG. 1. Particularly, this embodiment 1 is characterized in that an authentication means is installed in the right hand 60R at the end of the right arm 42R.

FIG. 3 is a schematic diagram for showing the right hand 60R of the humanoid robot of the embodiment 1. In this case, the right hand 60R consists of a palm member 62, a thumb member 64$t$, a first finger member 64$i$, a middle finger member 64$m$, a third finger member 64$r$ and a little finger member 64$f$. Each finger member is provided with joints located in three positions in the same manner as a human being, and a drive mechanism which independently drives the motion of each joint. Furthermore, each joint is provided with a joint position sensor, a torque sensor and an acceleration sensor, and capable of performing same motions as a human hand by driving each joint with reference to the information from these sensors. Particularly, the hand is structured to firmly shake hands by covering the hand of a partner (human being).

However, in this embodiment, the essential requirement of the operation to be implemented in the right hand 60R is the capability of shaking hands with a human being. Accordingly, there is no problem even if a united finger member is formed by joining together the first finger member 64$i$, the middle finger member 64$m$, the third finger member 64$r$ and the little finger member 64$f$. In this case, however, such a united finger member is provided with joints required for shaking hands with a human being and capable of being driven independently of the thumb member 64$t$.

Also, there are provided a near infrared sensor 74 at the center inside the palm member 62 of the right hand 60R, and a pair of near infrared LEDs 72$a$ and 72$b$ located also inside the palm member 62 with this near infrared sensor 74 therebetween (in the vertical direction of the figure). While the robot 100 is shaking hands with a human being, near infrared light is radiated from the near infrared LEDs 72$a$ and 72$b$. The near infrared light is passed through a near infrared window 76 to irradiate the inside of the respective fingers of a person shaking hands, i.e., a first finger 65i, a middle finger 65m, a third finger 65r and a little finger 65f, particularly, the inside of the middle finger 65m and the third finger 65r. The reflected light enters the near infrared sensor 74 which detects the reflected light and obtains the image data of veins.

There is a network of veins in a palm of a person where blood is circulating therethrough. The blood flowing in veins contains hemoglobin which absorbs near infrared light in the wavelength near 760 nm. Accordingly, it is possible to obtain a taken image, in which is blackened a vein pattern which weekly reflects light, by radiating near infrared light. This taken image is used to perform vein authentication.

In this case, the image data is analyzed to identify image areas corresponding to the first finger 65i, the middle finger 65m, the third finger 65r and the little finger 65f. Vein patterns are extracted from the image areas corresponding to the middle finger 65m and the third finger 65r. Accordingly, each of the middle finger 65m and the third finger 65r is used to performs vein authentication so that the accuracy is improved as compared with the case with only one finger.

Meanwhile, in the case of the humanoid robot of this embodiment 1, the left arm 42L and the right arm 42R are perfectly symmetric in the right and left direction so that a hand 60L at the end of the left arm 42L has the same structure as the right hand 60R. However, the authentication devices such as the near infrared LEDs 72a and 72b and the near infrared sensor 74 can be omitted from the left hand 60L so that authentication is performed always with the right hand 60R. In this case, if a left hand is extended by a person such as a left-handed person for hand shaking, the robot may say "Sorry, I identifies you by shaking hands with my right hand".

[Registration Process]

Next is an explanation of the registration process of the humanoid robot 100 in accordance with this embodiment. In the initial start after shipment, the humanoid robot 100 makes general greetings such as "Nice to meet you . . . ", and then says "Please let me know the name of my owner". The owner then answers to the humanoid robot 100, for example, "George". The humanoid robot 100 recognizes the answer by speech recognition and says "George, you are registered as an owner". The humanoid robot 100 says "Please let us shake hands for vein authentication". The owner starts an authentication process by shaking hands with the humanoid robot 100. This process will be explained with reference to a flow chart shown in FIG. 4.

First, in step S401, the humanoid robot 100 extends the right hand 60R to start a hand shaking motion. This hand shaking motion is a motion of changing to a state in which the humanoid robot 100 is shaking a hand of a person under a certain pressure. Accordingly, in step S402, it is detected by the joint position sensors whether or not the thumb member 64t is in a position corresponding to a shaking state in relation to the palm member 62 and the other finger members, and it is detected by the torque sensors whether or not a torque no smaller than a predetermined value is generated at each finger member in correspondence with the shaking state. It is determined by this process whether or not the right hand 60R has been shifted to the shaking state. If the right hand 60R is not shifted to the shaking state, after standing by for a predetermined time (for example, 100 milliseconds) in step S403, step S402 is performed again to confirm shifting to the shaking state. This is repeated until shifting to the shaking state is confirmed.

If it is determined in step S402 that the right hand 60R has been shifted to the shaking state, the process proceeds to step S404. In step S404, near infrared light is emitted from the near infrared LEDs 72a and 72b, and the near infrared sensor 74 acquires a taken image. For example, while three taken images are acquired successively with intervals of 100 milliseconds, these intervals are effectively utilized by performing a multitask consisting of an image taking thread and a data registration thread.

Namely, in this registration process, an image taking thread is first created. Each time taken image data is obtained by the near infrared sensor 74 in step S404, one data registration thread is created by the use of this taken image data. This data registration thread is a thread which performs step S410 to step S416. On the other hand, the image taking thread is a thread which can concurrently perform step S401 to step S408 while the data registration thread is performed.

When a data registration thread is created in step S404, it is determined in step S405 of the image taking thread whether or not a predetermined number of images (three images in this example) have been taken. If the predetermined number of images have not been taken yet, an image is taken again in step S404 after standing by for 100 milliseconds in step S406.

When it is determined in step S405 that the predetermined number of images (three images in this example) have been taken, the humanoid robot 100 changes the shaking hand position by changing the position of the hand 60R, shifting gripping positions of the fingers and so forth, followed by taking images again. This process is repeated a predetermined times.

Namely, it is determined in step S407 whether or not the process of acquiring taken images is repeated the predetermined times. If the process is not repeated the predetermined times yet, the process is repeated by changing the shaking hand position in step S408, shaking the hands again, stopping moving and taking images.

When it is determined in step S407 that the process of acquiring taken images is repeated the predetermined times, the image taking thread is completed in step S409 without taking a further image. The number of this predetermined times is, for example, three to five times so that 9 to 15 images are taken in total.

On the other hand, in the data registration thread which is created in step S404 each time one taken image is acquired, a vein data set is extracted from the taken image in step S410 and stored in an information recording device in step S411 as an owner registration data set.

Next, in step S412, it is determined whether or not the image taking thread has been completed. If the image taking thread has not been completed yet, in step S413, the current data registration thread is terminated here. If the image taking thread is completed in step S412, the above process is repeated once more to acquire a further vein data set. This is for the purpose of increasing accuracy by increasing registration data.

First, in step S414, it is determined whether or not re-acquisition has already been performed. If re-acquisition has already been performed, re-acquisition is not repeated so that all the process is finished. Conversely, if re-acquisition has not been performed yet, the humanoid robot opens the fingers of the hand 60R in step S415 to release the shaking state and take hands off temporarily, and says "Please shake my hand again" or the like. Then, the image taking thread is created again in step S416, and the current data registration thread is terminated. Thereafter, the above process is repeated from step S401 by the image taking thread which is created again.

The registration data acquired by the above process is recorded with the name "George" as a key, in association with the registration date and the current location obtained by GPS, in a vein database which is stored in a nonvolatile memory such as an EEPROM.

Incidentally, when a plurality of owners are registered, the similar procedure is repeatedly performed. For example, after completing the registration of one owner, the humanoid robot 100 says "Please let me know another owner". If the owner says "No further owner", "That's all" or the like, the process is finished.

[Authentication Process]

Next is an explanation of the authentication process (user identification process) which uses the above registration data set. For example, when starting up the humanoid robot 100 whose owner has already been registered, the humanoid robot 100 says first "Now, my system starts up. Please give me your hand to confirm the owner", and put out the hand. In what follows, this process will be explained with reference to a flow chart shown in FIG. 5.

First, in step S501, the humanoid robot 100 extends the right hand 60R to start a hand shaking motion. This hand shaking motion is a motion of changing to a state in which the humanoid robot 100 is shaking a hand of a person under a certain pressure. Accordingly, in the same manner as in the above registration process, in step S502, it is detected by the joint position sensors whether or not the thumb member 64t is in a position corresponding to a shaking state in relation to the palm member 62 and the other finger members, and it is detected by the torque sensors whether or not a torque no smaller than a predetermined value is generated at each finger member in correspondence with the shaking state. It is determined by this process whether or not the right hand 60R has been shifted to the shaking state. If the right hand 60R is not shifted to the shaking state, after standing by for a predetermined time (for example, 100 milliseconds) in step S503, step S502 is performed again to confirm shifting to the shaking state. This is repeated until shifting to the shaking state is confirmed.

If it is determined in step S502 that the right hand 60R has been shifted to the shaking state, the process proceeds to step S504. In step S504, near infrared light is emitted from the near infrared LEDs 72a and 72b, and the near infrared sensor 74 acquires a taken image. For example, while three taken images are acquired successively with intervals of 100 milliseconds, these intervals are effectively utilized by performing a multitask consisting of an image taking thread and an evaluation thread.

Namely, this process is started first as an image taking thread. Each time taken image data is obtained by the near infrared sensor 74 in step S504, one evaluation thread is created by the use of this taken image data. This evaluation thread is a thread which performs step S510 to step S520. On the other hand, the image taking thread is a thread which can concurrently perform step S501 to step S508 while the evaluation thread is performed.

When an evaluation thread is created in step S504, it is determined in step S505 of the image taking thread whether or not a predetermined number of images (three images in this example) have been taken. If the predetermined number of images have not been taken yet, an image is taken again in step S504 after standing by for 100 milliseconds in step S506.

When it is determined in step S505 that the predetermined number of images (three images in this example) have been taken, in the same manner as the registration process shown in FIG. 4, the humanoid robot 100 changes the shaking hand position by changing the position of the hand 60R, shifting gripping positions of the fingers, shaking hands again, stopping motion and so forth, followed by taking images again. This process is repeated a predetermined times. However, in this case, the number of this predetermined times is, for example, two to three times so that 6 to 9 images are taken in total. When it is determined in step S507 that the process of acquiring taken images is repeated the predetermined times, the image taking thread is completed in step S509 without taking a further image.

Also, as described above, each time one taken image is acquired in step S504, an evaluation thread is created, and the process proceeds to step S510. In step S510, a vein data set is extracted from the taken image and stored as a collation data set. The above process is similar as the process of acquiring registration data shown in FIG. 4.

Next, in step S511, one registration data set registered as owner data is acquired from the vein database. In step S512, this registration data set is compared and collated with the collation data set stored in step S510 to calculate a score which indicates a similarity degree therebetween.

In step S513, it is determined whether or not the calculated score is greater than a predetermined threshold value. If the calculated score is greater than the predetermined threshold value, the person shaking hands is authenticated as the owner to terminate this process with a result of authentication success.

The collation data set corresponding to the authentication success is then added to the vein database as a new registration data set. When the number of registration data sets registered in the vein database exceeds a predetermined number (for example, 32 sets), a registration data set having a minimum correlation value with the other registration data sets is deleted.

Conversely, if the calculated score is not greater than the predetermined threshold value, the process proceeds to step S515. In this step S515, it is determined whether or not there is a next registration data set. If there is a next registration data set, the process is returned to step S511 to perform the process again with this next registration data set.

Conversely, if there is no next registration data set, i.e., if all the registration data sets have been processed, the process proceeds to step S516. In step S516, it is determined whether or not the image taking thread has been completed. If the image taking thread has not been completed yet, in step S513, the current evaluation thread is terminated here.

If the image taking thread is completed in step S516, the authentication is recognized to be unsuccessful. However, the unsuccessful authentication may have resulted from an inappropriate handshaking position, and therefore authentication might be successfully performed if performing handshaking again. Accordingly, a retry is performed one more time.

First, in step S518, it is determined whether or not a retry has already been performed. If a retry has already been performed, since a retry is performed only once, this process is finished, resulting in authentication failure. In this case, the humanoid robot 100 may explain, for example, by saying "Since the owner cannot be confirmed, operation is started in a restriction mode".

If no retry has been performed yet, the humanoid robot opens the fingers of the hand 60R in step S519 to release the shaking state and take hands off temporarily, and says "Please shake my hand again" or the like. Then, the image taking thread is created again in step S520, and the current evaluation thread is terminated. Thereafter, the above process is repeated from step S501 by the image taking thread which is created again.

Meanwhile, in the case where there are many registration data sets, evaluation takes time so that, in advance of terminating one evaluation thread, the next evaluation thread may be started. In such a case, parallel processing is performed between the evaluation threads. However, if there is little advantage in such parallel processing between evaluation threads (for example, if the information processing apparatus is implemented with a single processor), the next evaluation thread may be on standby, and started only after the preceding evaluation thread ends. Also, while a retry is performed only once in the above process, it is possible to repeat the retry plural times.

In the case where an individual owner is identified as described above, the robot operates in an owner operation mode in which there is basically no restriction on operation of the robot. If no individual owner is identified, the robot operates in a restriction mode. For example, in the case where life log of the individual owner or the like is asked, if the robot is in the owner operation mode, an answer is given, but otherwise the robot says "That is personal information, and cannot be answered" or the like. Furthermore, even if an owner is identified, when it is known by the image sensors of the left and right eyes 52L and 52R that there is another person, the robot may operate in a restriction mode.

Also, in the case where it is confirmed by GPS that the current location is far remote from owner's home, the operation mode is preferably switched from the owner operation mode to the restriction mode when a predetermined period elapses after owner authentication is performed as described above. This is for the purpose of protecting owner's privacy and the like when someone else moves the robot to a place remote from owner's home.

In accordance with this scheme, the operation mode may be switched to the restriction mode when the owner himself goes out with the robot. Accordingly, the above owner authentication has to be performed again when the owner operation mode is needed. In such a case, the authentication process is started by saying "Let's shake hands" to the humanoid robot 100 operating in the restriction mode.

[Embodiment 2]

The embodiment 1 shown in FIG. 3 as described above is based on the so-called finger vein authentication which is performed by examining veins of fingers of a person who is shaking hands. In this case, the two fingers of the middle finger 65m and the third finger 65r are used to performs vein authentication so that a higher accuracy can be expected. In addition to this, since near infrared light is radiated in parallel with the palm of a hand, the focal length of an optical system can be long, and therefore it is characterized in that images with little distorsion can be obtained.

However, since the fingers are bent when shaking hands, the vein pattern thereof tends to be distorted in comparison with the vein pattern obtained when the fingers are stretched straight. The registration data and the collation data correspond with respect to this distortion, so that there is no problem in collation itself. However, because of different bending states, position displacement and the like of the shaking hand, image processing becomes necessary for image correction to place a heavy load on software.

Figure 6:
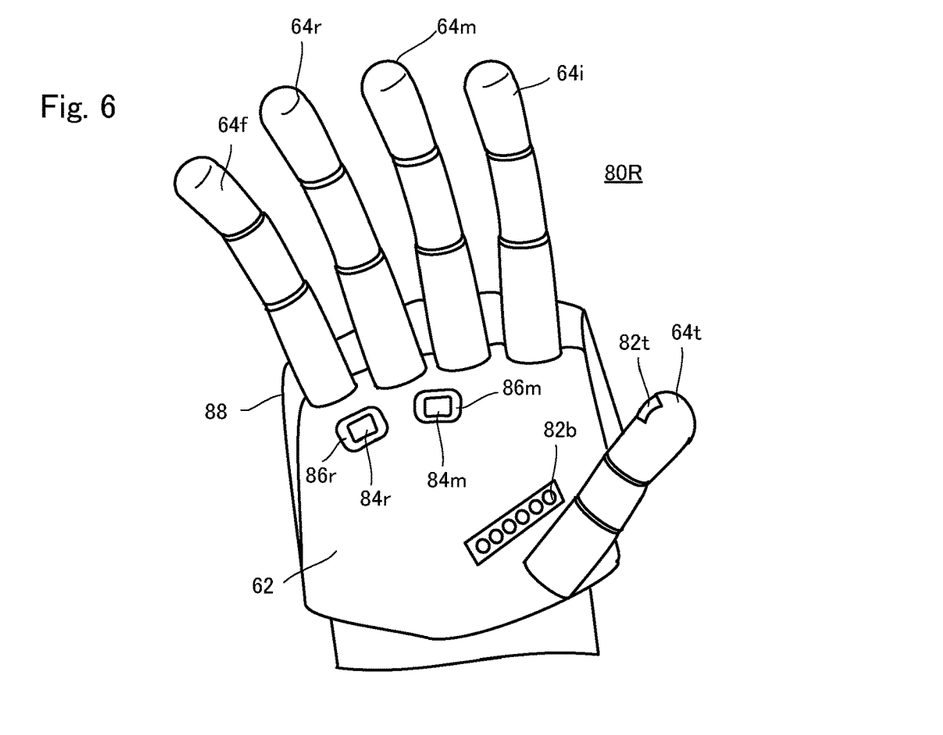
FIG. 6 is a schematic diagram for showing the structure of a hand of a humanoid robot of an embodiment 2 of the present invention.

Accordingly, in the case of the embodiment 2, a palm authentication is used in place of the finger vein authentication. FIG. 6 is a schematic diagram for showing a hand 80R of the humanoid robot of the embodiment 2. Except for the elements relating to vein authentication, the basic elements of the hand 80R are similar to those of the hand 60R of the humanoid robot shown in FIG. 3, and therefore no redundant description is repeated while like reference numbers indicate functionally similar elements.

In this embodiment 2, there are provided a plurality of the near infrared LED 82b linearly arranged near the base of the thumb member 64t of the hand 80R, and near infrared sensors 84m and 84r near the bases of the middle finger member 64m and the third finger member 64r respectively. Furthermore, there are a plurality of the near infrared LED 82t inside the tip of the thumb member 64t. Also, there is a shading cover 88 for the purpose of reducing external light which may enter the near infrared sensors 84m and 84r.

Figure 7:
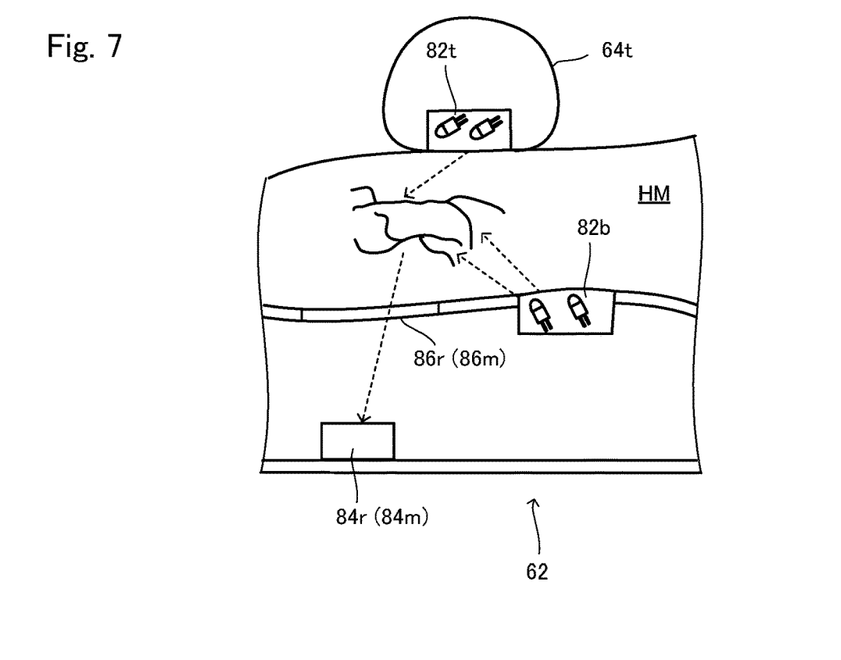
FIG. 7 is a view for explaining the situation in which veins are imaged while the humanoid robot of the embodiment 2 of the present invention is shaking hands.

While the robot is shaking hands, near infrared light is radiated from the near infrared LEDs 82b and 82t (refer to FIG. 7). This near infrared light irradiates the inside of the palm member HM of a person shaking hands. The reflected light thereof is passed through near infrared windows 86m and 86r to enter the near infrared sensors 84m and 84r, detected by the near infrared sensors 84m and 84r, and taken as image data of veins. This taken image is used to perform palm authentication.

Since the registration process and authentication process of the humanoid robot 100 in accordance with this embodiment are basically same as those of the embodiment 1 shown in FIG. 4 and FIG. 5, no redundant description is repeated. However, since there are the two near infrared sensors 84m and 84r which acquire taken images respectively, the number of taken images is twice that of the embodiment 1. The number of the collation data sets also becomes twice so that a higher accuracy can thereby be expected.

[Embodiment 3]

In accordance with this embodiment, in addition to the owner of the robot shown in the embodiment 1 or the embodiment 2, a person who is not an owner is also identified. The hardware of this humanoid robot is the same as that of the embodiment 1 or the embodiment 2 and structured to firmly shake hands by covering the hand of a partner (human being).

When identifying a person with the image sensors of the left and right eyes 52L and 52R to recognize an encounter with the person, this humanoid robot greets the person by saying "Hello, I am Robo, a humanoid robot". If the person knows that the humanoid robot performs personal identification through a handshake and desires it, the person starts an identification process by saying "Robo, let's shake hands".

Figure 8:
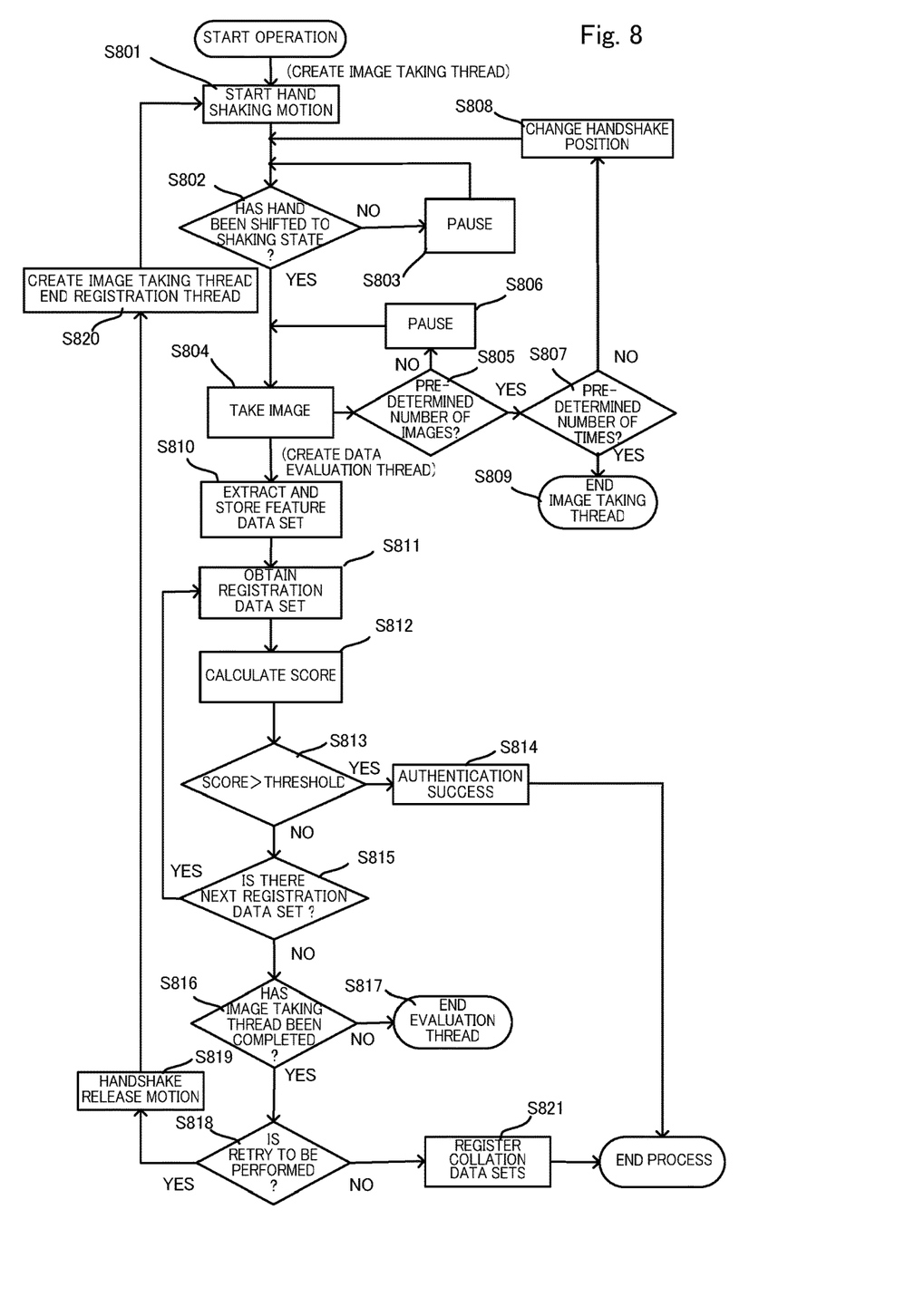
FIG. 8 is a flow chart for showing the procedure of performing identification of the person in accordance with the embodiment 1

In what follows, this identification process will be explained with reference to a flow chart of FIG. 8. In this case, an owner and another person, who is not an owner, are handled by the similar process for identification. However, since many vein data sets are registered and used in the case of an owner as described above, the identification accuracy of the owner is relatively high as compared with that of another person. Also, the vein data sets of the owner are used first. When an owner is not surely identified but seems to be identified with a high probability, a retry is performed through step S519 and step S520 shown in FIG. 5. Contrary to this, in the case of the vein data sets of a person who is not an owner, the identification process is performed only once. Furthermore, if an owner is identified, the operation mode is switched to the owner operation mode.

First, in step S801, the humanoid robot extends the right hand 60R to start hand a shaking motion. This hand shaking motion is a motion of changing to a state in which the humanoid robot 100 is shaking a hand of a person under a certain pressure. Also in this case, while standing by for a predetermined time (for example, 100 milliseconds) in step S803 in the same manner as in the embodiment of FIG. 5, it is determined in step S802 whether or not the right hand 60R has been shifted to the shaking state.

If it is determined in step S802 that the right hand 60R has been shifted to the shaking state, the process proceeds to step S804. In step S804, near infrared light is emitted from the near infrared LEDs 72b and 72t, and the near infrared sensors 74m and 74r acquires taken images. For example, while three taken images are acquired successively with intervals of 100 milliseconds for each near infrared sensor, these intervals are effectively utilized by performing a multitask consisting of an image taking thread and an evaluation thread in the same manner as in the embodiment of FIG. 5.

Namely, in this registration process, an image taking thread is first created. Each time taken image data is obtained by the near infrared sensors 74m and 74r in step S804, one evaluation thread is created by the use of this taken image data. This evaluation thread is a thread which performs step S810 to step S820. On the other hand, the image taking thread is a thread which can concurrently perform step S801 to step S808 while the evaluation thread is performed.

When an evaluation thread is created in step S804, it is determined in step S805 of the image taking thread whether or not a predetermined number of images have been taken. If the predetermined number of images have not been taken yet, an image is taken again in step S804 after standing by for 100 milliseconds in step S806. Incidentally, for example, the predetermined number is three in the case of the embodiment 1, and three for each near infrared sensor in the case of the embodiment 2.

When it is determined in step S805 that the predetermined number of images have been taken, in the same manner as the registration process shown in FIG. 4, the humanoid robot 100 changes the shaking hand position by changing the position of the hand 60R, shifting gripping positions of the fingers, shaking hands again, stopping motion and so forth, followed by taking images again. This process is repeated a predetermined times. However, in this case, the number of this predetermined times is, for example, two or three times. Accordingly, the number of taken images which are acquired is six to nine in the case of the embodiment 1, and six to nine for each near infrared sensor, i.e., 12 to 18 in total in the case of the embodiment 2. When it is determined in step S807 that the process of acquiring taken images is repeated the predetermined times, the image taking thread is completed in step S809 without taking a further image.

Also, as described above, each time one taken image is acquired in step S804, an evaluation thread is created, and the process proceeds to step S810. In step S810, a vein data set is extracted from the taken image and stored as a collation data set. The above process is similar as the process of acquiring registration data shown in FIG. 5 and FIG. 4.

Next, in step S811, one registration data set is acquired from the vein database. As has been discussed above, in this case, the vein data sets of the owner are acquired first. In step S812, this registration data set is compared and collated with the collation data set stored in step S810 to calculate a score which indicates a similarity degree therebetween.

In step S813, it is determined whether or not the calculated score is greater than a predetermined threshold value. If the calculated score is greater than the predetermined threshold value, the person shaking hands is personally identified to terminate this process with a result of personal identification success. In this case, for example, the humanoid robot says "You are George" by making use of the personal name which is identified. The humanoid robot may thereafter behave on the basis of the result of personal identification. Then, in the same manner as in step S514, the vein database is updated with this collation data set.

Conversely, if the calculated score is not greater than the predetermined threshold value, the process proceeds to step S815. In this step S815, it is determined whether or not there is a next registration data set. If there is a next registration data set, the process is returned to step S811 to perform the process again with this next registration data set.

Conversely, if there is no next registration data set, i.e., if all the registration data sets have been processed, the process proceeds to step S816. In step S816, it is determined whether or not the image taking thread has been completed. If the image taking thread has not been completed yet, in step S813, the current evaluation thread is terminated here.

If the image taking thread is completed in step S816, the authentication is recognized to be unsuccessful. When an owner is not surely identified but seems to be identified with a high probability, a retry is performed in the same manner as in the embodiment shown in FIG. 5. Specifically, if it is determined in step S813 that the calculated score is not higher than a predetermined threshold value (first threshold value) but if scores calculated with all the registration data sets seem relatively high, a retry is performed. For example, if there is a score which is higher than a second threshold value which is lower than the first threshold value, a retry is performed one more time.

Namely, in step S818, it is determined whether a retry is to be performed. Namely, if the condition that step S818 is not performed in the retry process and the condition that a score obtained by collation with an owner registration data is higher than the second threshold value are satisfied, it is determined to perform a retry.

If it is determined that a retry is to be performed, the humanoid robot opens the fingers of the hand 60R in step S819 to release the shaking state and take hands off temporarily, and says "Please shake my hand again" or the like. Then, the image taking thread is created again in step S820, and the current evaluation thread is terminated. Thereafter, the above process is repeated from step S801 by the image taking thread which is created again.

If it is determined that a retry is not to be performed, the authentication is unsuccessful. In such a case, the humanoid robot says "Could I have your name?". For example, if the person replies, "Bob", the above plurality of collation data sets are registered in association with "Bob" as a name in step S821.

[Embodiment 4]

This embodiment is characterized in that, while performing vein authentication, a heart rate is also measured. The measured heart rate is utilized as reference information for identity confirmation, or notified to the person. For example, in the case where the determination of the vein authentication is on the borderline between success and failure, if the measured heart rate coincides, the authentication may succeed because the possibility of being the person is raised. Alternatively, the humanoid robot serves as a heart rate meter. Incidentally, except for the elements relating to the heart rate measurement, the basic elements of this embodiment are similar to those of the embodiment 1 or the embodiment 2, and therefore no redundant description is repeated.

Veins are located near the surface of skin (about 1.5 mm to 2.0 mm). Accordingly, a vein pattern can be imaged by setting the focal point of the optical system of the near infrared sensor to this location in order to effectively collect light which is passed through the veins. On the other hand, arteries are located more inside than veins, and also absorb near infrared light.

While veins hardly pulsate, arteries pulsate to periodically change the sizes thereof in correspondence with the heart rate. Accordingly, periodical variation due to the pulsation is reflected in the signal level of near infrared light entering the near infrared sensor. The heart rate can be measured by calculating the average signal level of the output of the near infrared sensor for each measurement, extracting a predetermined frequency range from the average signal levels through a band pass filter implemented with a digital filter or the like.

In the case of the specific example of the above embodiment, imaging is repeated three times with intervals of 100 milliseconds. However, in the case of the present embodiment, imaging is continuously repeated with intervals of 100 milliseconds as long as handshake continues. The heart rate can be identified by calculating the average signal level of each of all the images, which are taken, and Fourier transforming the average signal levels to identify a cycle corresponding to the heart rate.

When sampling with intervals of 100 milliseconds, the heart rate can be measured up to 300 per minute. The maximum heart rate of human beings is about 200, and therefore this sampling rate will be sufficient. The precision may be increased by increasing the sampling rate and removing high frequency components. However, it is usually conceived that such high frequency components can be neglected. Also, frequency components of 30/min or lower can be considered to originate from body motions, fluctuation of a heart rate or the like. However, the influence of body motions on the signal level of near infrared light is thought to be small. On the other hand, since the timely range of measurement is limited, the fluctuation of a heart rate is thought to be neglected as compared with the precision as required.

For this reason, a bandpass filter is not used in this embodiment. Namely, the heart rate can be calculated by spatially averaging the signal levels of near infrared light entering the near infrared sensor, Fourier transforming the average signal levels obtained with interval of 100 milliseconds, and identifying a maximum frequency component from the result of the Fourier transform. Specifically, handshake is continued for seven seconds to collect 64 data items, which are Fourier transformed (FFT).

However, for example, 256 data items may be collected after the purpose of collection is notified in advance by saying "Heart rate is measured. Please hold still for about 30 seconds while shaking hands". In this case, the heart rate can be measured with a higher degree of precision. Meanwhile, in the case where many samples are taken for measuring the heart rate, vein authentication is performed by selecting three images having greater contrast differences, i.e., three more focused images from among taken images.

[Embodiment 5]

Figure 9:
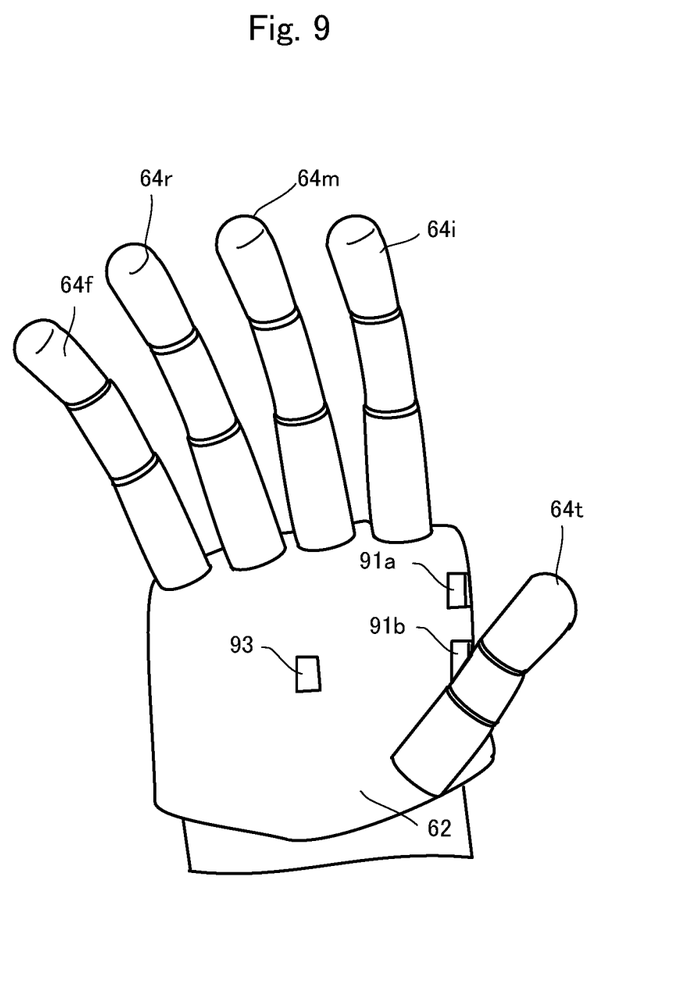
FIG. 9 is a schematic diagram for showing the structure of a hand of a humanoid robot of an embodiment 5 of the present invention.

In this embodiment, sensors for collecting biological information are further provided in the hand of the humanoid robot of any one of the embodiment 1 through the embodiment 4. As illustrated in FIG. 9, in this case, there are provided force sensors 91*a* and 91*b* for measuring a gripping force while shaking hands, and a temperature sensor 93 for measuring a body temperature.

The force sensors 91*a* and 91*b* are sensors of a piezo type, a strain gauge type or the like and located in such positions as to surely receive the gripping force when shaking hands, e.g., two positions in the direction toward the first finger member 64*i* from the base of the thumb member 64*t*. The temporal change of a gripping force (gripping force pattern) is recorded as the output of each force sensor until the hand shaking state is stabilized after starting the hand shaking.

Since the plurality of force sensors are located in different positions as described above, it is possible to absorb fluctuations, even if the hand shaking position slightly changes, by using a greatest measurement value as a representative value. Also, the hand shaking habit of a person can be recorded to some extent and acquired as correlation values by associating the temporal changes of a gripping force at the locations with each other.

Also, the temperature sensor 93 is a temperature sensor implemented for example with a thermistor device and located near the center of the palm member 62. The temperature of skin of the hand is measured while shaking hands. The temperature which is measured is not a body temperature as it is. However, reference information is given thereby about the skin temperature of the person.

When authentication has succeeded through handshake, a gripping force pattern and the measured skin temperature are recorded as biological information data. Also, for example, in the case where the determination of the vein authentication is on the borderline between success and failure, if the gripping force pattern and the skin temperature as measured approximately coincide with past recorded data, the robot makes the authentication succeed. Namely, the joint position pattern can be used as auxiliary information for use in the identity confirmation.

In addition to this, when the gripping force is greater than that measured in the past, the robot may say "Today, you look like you are doing well". Conversely, when the gripping force is weaker than that measured in the past, the robot may say "How are you feeling today?". Likewise, when the skin temperature is high, the robot may say "Have you any fever?".

The biological information data is successively stored as reference data. However, when the number of data items exceeds a certain number, the data items are deleted from one having the greatest deviation from the average value. Accordingly, while repeating authentication, the stored biological information data can be optimized.

[Embodiment 6]

In this embodiment, while performing vein authentication, information about the profile of a hand is also acquired. Namely, while predetermined torques are being detected by the torque sensors of the respective fingers, i.e., the thumb member 64*t*, the first finger member 64*i*, the middle finger member 68*m*, the third finger member 64*r* and the little finger member 64*f*, the outputs of the joint position sensors are recorded. The pattern of these joint positions is thought to reflect the profile of the hand of the person shaking hands.

When authentication succeeds, the joint position pattern at this time is recorded as data representing the profile of the hand of the person. Also, for example, in the case where the determination of the vein authentication is on the borderline between success and failure, if the joint position pattern as detected approximately coincide with past recorded data, the robot makes the authentication succeed. Namely, the joint position pattern can be used as auxiliary information for use in the identity confirmation.

Also, if the number of the joint position patterns obtained when authentication succeeded exceeds a certain number, the patterns are deleted from one having the greatest deviation from the average value. Accordingly, while repeating authentication, the joint position patterns can be optimized.

[Embodiment 7]

In this embodiment, the above vein authentication is combined with other types of authentication techniques. For example, formants of a registrant (owner) is registered for voiceprint authentication before, after or during the registration process for vein authentication of the embodiment 1. Formants forms a pattern of maximum frequencies of a voice signal. This voiceprint pattern is related to the shape of a vocal tract so that it is difficult to imitate it. In addition to this, characteristics of intonations and accents, an utterance level, a speaking speed and the like are registered.

This can be performed by recording voices of a free talk during performing vein authentication, and analyzing the voices to calculate formants. By this method, formants can quite naturally be acquired. The accuracy can be improved by having the person speak an appropriate keyword or phrase, which is determined in advance to register formants.

The identity confirmation with a voiceprint pattern is performed by recording voices and collating the recorded voices with a registered voiceprint pattern before, after or during the registration process for vein authentication. The collation result is reflected in the score of the vein authentication.

Incidentally, while performing communication, this humanoid robot always performs speech recognition. Usually, this speech recognition results are not necessarily stored, but preferably stored separately for each speech partner in a database. For example, while making voice conversation, the conversation content as text is morpheme analyzed, and compared with content of the database, and it is determined that the speech partner is likely to be a user if the database contains many conversation contents associated with the user and similar to the morpheme analyzed content. In this case, since the accuracy is not high, it can be used as a communication pattern such as saying "Are you perhaps Mr. ○ ○?"

Also, face authentication data is registered before, after or during the registration process for vein authentication. For example, while performing vein authentication registration, formants for voiceprint authentication are acquired during freely talking, and at the same time face images are collected. Feature points are extracted from the face images and registered. Specifically, sizes and relative displacements among parts of a face, and the profiles of eyes, a nose, a cheekbone and jaws are used as feature points.

The voiceprint authentication and the face authentication have lower accuracy than the vein authentication. The authentication based on conversation content seems to have a further lower accuracy. However, in the case where the accuracy of the vein authentication is lowered for some reason, these authentication methods have complementary roles. The voiceprint authentication, the face authentication and the authentication based on conversation content make use of information resources which are entirely different from the information resource which are used by the vein authentication. When there is doubt as to the reliability of the vein authentication because of fraudulent acts or the like, these complementary authentications becomes substantially effective for security reasons.

On the other hand, having a higher accuracy, the vein authentication takes time to perform a sequence of processing because of referencing a database or the like. Accordingly, authentication is first performed by one or any combination of the voiceprint authentication, the face authentication and the authentication based on conversation content, and when some definite result cannot be obtained therefrom, the vein authentication may be performed next.

Alternatively, when a security related operation is performed such as answering a question relating to personal information, for example, a question relating to a life log of an individual owner, the vein authentication may be performed from the biginining. Otherwise, one or any combination of the voiceprint authentication, the face authentication and the authentication based on conversation content may be first performed.

The foregoing description of the embodiments has been presented for purposes of illustration and description. It is not intended to be exhaustive or to limit the invention to the precise form described, and obviously many modifications and variations are possible in light of the above teaching. The embodiment was chosen in order to explain most clearly the principles of the invention and its practical application thereby to enable others in the art to utilize most effectively the invention in various embodiments and with various modifications as are suited to the particular use contemplated.

For example, when the score calculated in step S513 or step S813 is greater than the predetermined threshold value, the authentication of an individual succeeds and the process is finished. However, if the number of registration data sets registered in the vein database exceeds a predetermined number (for example, 32 sets), the calculation of a score may be continuously repeated throughout all the registration data sets associated with the individual. Thereafter, after deleting the registration data set having the lowest score, the collation data set is added as a new registration data set in place of the deleted registration data set. In this way, it is possible to delete a registration data set having small correlation from among the registration data sets registered in the vein database with a small calculation amount.

INDUSTRIAL APPLICABILITY

As has been discussed above, in accordance with the humanoid robot of the present invention, it is possible to inhibit theft of the humanoid robot and reflect identification of an individual in the behaviour of the humanoid robot by identifying the individual through handshake which is a natural motion of a person. Accordingly, the value of the humanoid robot itself is increased.

EXPLANATION OF SYMBOLS

10 information processing apparatus
14 timer
15 control circuit
16 base
17 drive motor control circuit
22L left leg
22R right leg
30 torso
42L left arm
42R right arm
50 head
52L, 52R eye
54L, 54R ear
56 nose
58 mouth
60L left hand
60R right hand
62 palm member
64*f* little finger member
64*i* first finger member
64*r* third finger member 64t thumb member
64m middle finger member
65f little finger
65i first finger
65m middle finger
65r third finger
72b, 72t near infrared LED
74m, 74r near infrared sensor
76m, 76r near infrared window
80R hand
84m, 84r near infrared sensor
86m, 86r near infrared window
88 shading cover
91a, 91b force sensor
100 humanoid robot

The invention claimed is:

1. A humanoid robot comprising:
a hand having a plurality of finger members provided with joints and drive mechanisms and capable of performing a handshake with a hand of a human being;
a joint position sensor configured to detect a position of at least one of the joints;
an information recording device configured to record the joint position detected by the joint position sensor; and
an information processing apparatus configured to compare the joint position of the hand of the human being recorded in the information recording device in advance and the joint position detected by the joint position sensor when shaking a hand of a human being to be personally identified, wherein
the joint position comparison result by the information processing apparatus is used to perform personal identification of the human being.

2. The humanoid robot of claim 1, wherein the joint position sensor is provided for each of the plurality of finger members, wherein the profile of the hand is represented by the pattern of the plurality of the joint positions detected by the joint position sensors, and wherein the information processing apparatus compares the joint position pattern of the human being recorded in the information recording device and the joint position pattern detected by the joint position sensor when shaking a hand of a human being to be personally identified.

3. The humanoid robot of claim 1, further comprising a force sensor which is provided in the hand of the humanoid robot to measure a gripping force while performing a handshake, wherein the information recording device records the gripping force measured by the force sensor, wherein
the information processing apparatus compares the gripping force of the hand of the human being recorded in the information recording device in advance and the gripping force measured when shaking a hand of a human being to be personally identified, and wherein
the gripping force comparison result by the information processing apparatus is used to perform personal identification of the human being.

4. The humanoid robot of claim 1, further comprising:
a near infrared light emitting device and a near infrared sensor which are installed in the hand of the humanoid robot and located in such positions that, while the hand of the humanoid robot is shaking the hand of the human being, near infrared light emitted from the near infrared light emitting device irradiates the inside of the hand of the human being and is detected by the near infrared sensor as a vein pattern, wherein
the information recording device records the vein pattern detected by the near infrared sensor, and wherein
the information processing apparatus controls the motion of the hand of the humanoid robot to shake the hand of the human being, acquires a vein pattern by the near infrared light emitting device and the near infrared sensor as a collation data set, calculates the similarity degree between this vein pattern and the vein pattern which is recorded in advance as a registration data set in the information recording device, and performs personal identification of the human being on the basis of this similarity degree.

5. The humanoid robot of claim 4, wherein the vein pattern which is recorded as a registration data set is a vein pattern of an owner of the humanoid robot, and owner authentication is performed on the basis of the similarity degree between this vein pattern and the collation data set.

6. The humanoid robot of claim 5, wherein the registration data set is repeatedly acquired while changing the position of the hand of the humanoid robot.

7. The humanoid robot of claim 6, wherein, after acquiring the registration data set, the hand of the humanoid robot is released from the hand of the human being and shakes the hand of the human being again to acquire the registration data set again, and wherein both the previous registration data set and the registration data set acquired again are used as the registration data sets for performing personal identification by comparing and processing the registration data sets with the collation data set.

8. The humanoid robot of claim 7, wherein the result of personal identification is reflected in the behaviour of the humanoid robot.

9. The humanoid robot of claim 8, wherein the vein pattern is a vein pattern of a finger of the human being.

* * * * *